United States Patent [19]

Krushel

[11] Patent Number: 4,773,906
[45] Date of Patent: Sep. 27, 1988

[54] DIAPER

[76] Inventor: Sharon Krushel, 7117 - 100 Street, Peace River, Alberta, Canada, T0H 2X0

[21] Appl. No.: 936,545

[22] Filed: Dec. 1, 1986

[51] Int. Cl.$^4$ ............................................. A61F 13/16
[52] U.S. Cl. .................................................... 604/391
[58] Field of Search ............ 604/397, 398, 391, 385.1

[56] References Cited

U.S. PATENT DOCUMENTS

| 2,705,010 | 3/1955 | Sires | 604/397 |
| 2,733,715 | 2/1956 | Folk | 604/398 |
| 3,407,813 | 10/1968 | Grippo et al. | 604/398 |
| 3,828,785 | 8/1974 | Gamm et al. | 604/397 |
| 4,496,360 | 1/1985 | Joffe et al. | 604/397 |
| 4,568,342 | 2/1986 | Davis | 604/391 |
| 4,576,601 | 3/1986 | Brain | 604/398 |

Primary Examiner—John D. Yasko
Attorney, Agent, or Firm—Harold H. Dutton, Jr.; George H. Dunsmuir

[57] ABSTRACT

In a reusable diaper, it is known to sew layered absorbent material together and apply a variable width fastening system to make an absorbent diaper which does not require folding or pinning. A structurally simple, multi-layered diaper includes a generally rectangular absorbent panel with one flaring end and a pair of laterally extending arms at the other end thereof, a pair of parallel, laterally extending fastener strips on the outer surface of the flared end of the panel to facilitate adjustment in width and length, fastener tabs on the inner surfaces of the arms for coupling with one of the fastener strips to secure the diaper in the use position; and an auxiliary pad, one or both ends of which are connected to the inner surface of the panel, whereby air can circulate around the pad to facilitate faster drying of the laundered diaper.

5 Claims, 2 Drawing Sheets

DIAPER

BACKGROUND OF THE INVENTION

This invention relates to a diaper, and in particular to a reusable diaper of the type commonly used on children.

A diaper can be disposable or reusable. The most common disposable diapers consist of a waterproof outer layer, an absorbent core, and a relatively non-absorbent inner layer to conform to the body of the child. Examples of disposable diapers are found in U.S. Pat. Nos. 3,924,626, which issued to Gerald A. Lee et al on Dec. 9, 1975; 3,926,189, which issued to Glenn N. Taylor on Dec. 16, 1975; 4,037,602, which issued to Janet R. Hawthorne on July 26, 1977 and 4,578,071, which issued to Kenneth B. Buell on Mar. 25, 1986.

Various attempts have been made to incorporate some of the better features of disposable diapers in reusable diapers. Examples of reusable diaper structures are found in U.S. Pat. Nos. 4,300,563, which issued to Helen K. Brookfield on Nov. 17, 1981; 4,402,690, which issued to Robin Redfern on Sept. 6, 1983 and 4,568,342, which issued to Culley W. Davis on Feb. 4, 1986.

A common problem with such diapers is that while the fastener devices used in the diapers are adapted to fit around waists of various sizes, the length of the diaper remains constant. This means that the diaper will either extend a long way up the body of an infant or resemble a bikini on a large child. The alternative is to make the diapers available in various sizes, resulting in more expense to parents who will require dozens of diapers in each size.

Another problem inherent in reusable, multi-layered diapers relates to the number of layers required to make a relatively absorbent diaper. A diaper consisting of as many as eight layers of cotton flannelette does not match the absorbency capacity of the average disposable diaper. As layers are added to increase absorbency, drying time for the laundered diaper is increased as layers are sandwiched between continuous outer plies or layers of material and air circulation to the inner layers is greatly inhibited. This increased drying time is an inconvenience if the diapers are hung to dry and raises utility costs if the diapers are dried in an automatic clothes dryer. An alternative is to apply two diapers at a time or a diaper and a separate absorbent liner to the child but these alternatives are less convenient than the present invention.

The object of the present invention is to overcome the above-identified problems by providing a convenient multi-layered reusable diaper, adjustable in width and length, which is relatively absorbent and which dries relatively quickly.

SUMMARY OF THE INVENTION

Accordingly, the present invention relates to a reusable diaper comprising substantially rectangular absorbent panel means having one flared end; arm means extending outwardly from each side of the other end of said panel means; fastener means on said arm means for connecting said arm means to said one end when the diaper is in the folded, use position; absorbent pad means narrower than said panel means, at least one end of said pad means being connected to said panel means, whereby said pad means overlies the inner surface of said panel means in the use position, and the sides of said pad means are free to facilitate drying of the diaper after it has been washed.

BRIEF DESCRIPTION OF THE DRAWING

The invention will be described in greater detail with reference to the accompanying drawings, which illustrate a preferred embodiment of the invention, and wherein.

DESCRIPTION OF THE PREFERRED EMBODIMENT

Figure 1:
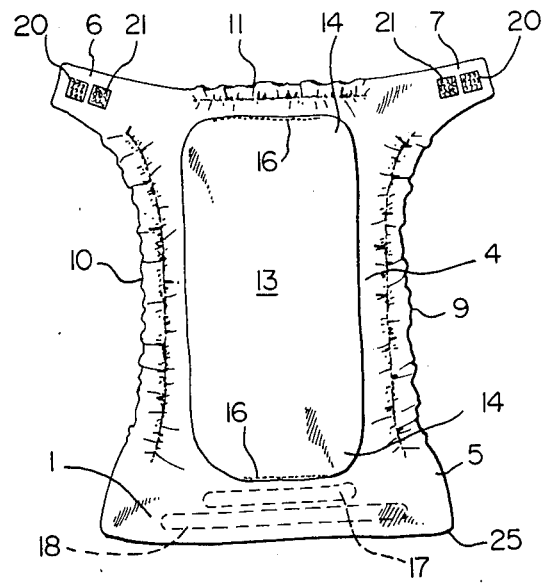
FIG. 1 is a plan view of the inner surface of a diaper in accordance with the present invention.

With reference to the drawings, the diaper of the present invention includes a pair of thin inner and outer layers 1 and 2, respectively of absorbent material, which define a generally rectangular panel 4 with one flared end 5 and a pair of outwardly extending arms 6 and 7 at the other end thereof.

Two layers of absorbent material (not shown), shorter and narrower than the panel, are sewn to the inside of layer 1.

The layers 1 and 2 are interconnected by stitching (not shown) extending along the entire periphery of the panel 4. The layers 1 and 2 are gathered along each side edge 9 and 10 thereof by being sewn to elongated (as in "stretched") strips (not shown) of elastic material, so that such side edges 9 and 10 can be stretched and will tend return to the rest position shown in FIGS. 1 to 3. Similarly, the top edge 11 is sewn to an elongated (as in "stretched") strip (not shown) of elastic material for ensuring a snug fit around the waist of a user.

A separate absorbent, generally rectangular pad 13 is provided on the inner surface of the panel 4. The ends 14 of the pad 13 are connected to the panel 4 by lines of stitching 16. Thus, the pad 13 is free to move away from the panel (FIG. 3) in order to facilitate faster drying of the laundered diaper. The ends 14 of the pad 13 are connected to the panel 4 so that the panel can be stretched longitudinally to its full length.

In use, the diaper is placed beneath a child, with the pad 13 uppermost (FIG. 1). The flared end 5 of the diaper is folded between the legs and brought into position over the stomach of the child. One lower fastener strip 17, and additional upper fastener strips 18 are provided on the outer surface of the flared end 5 of the panel 4. Thus, when the diaper is in the folded, use position (FIGS. 4 and 5), the strips 17 and 18 appear on the outer top front surface of the diaper. The fabric strips 17 and 18 define the loop portions of Velcro (trade mark) fasteners. The hook portions of the Velcro fasteners are defined by tabs 20 on the outer ends of the arms 6 and 7. Velcro loop tabs 21 are provided on the inner surfaces of the arms 21 inwardly of the hook tabs 20. A third Velcro loop tab 23 is provided on the outer surface of the arm 7.

Figure 4:
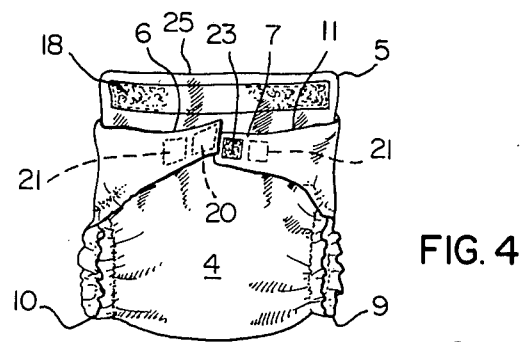
FIG. 4 is a front elevation view of the diaper of FIGS. 1 to 3 in one closed position.
Figure 5:
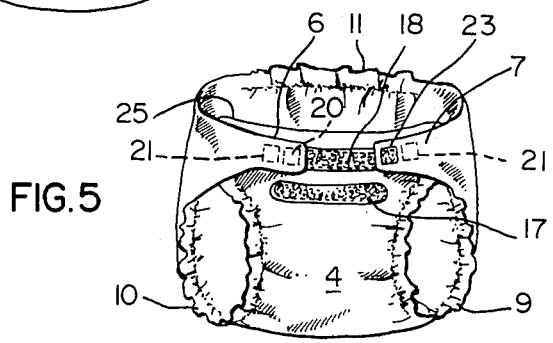
FIG. 5 is a front elevation view of the diaper of FIGS. 1 to 3 in a second closed position.

In order to fasten the diaper on a small child or infant, the flared end 5 of the panel 4 is folded into vertically overlapping relationship with the top edge 11 of the panel, so that the arms 6 and 7 are roughly aligned with the Velcro loop fabric strip 17. The arms 6 and 7 are then folded into overlapping relationship, so that the hook tab 20 on the arm 7 engages and releasably locks with the strip 17, and the hook tab 20 on the arm 6 engages and releasably locks with the tab 23 on the outer surface of the arm 7 (FIG. 4). The arms 6 and 7 may not overlap, in which case both of the tabs 20 are pressed into engagement with the strip 17 at spaced apart locations. While the edge 25 of the flared end 5 of the panel 4 is shown as being located a substantial distance above the top edge 11 of the front of the diaper, in fact, during use the edge 25 is folded downwardly and forwardly over the arms 6 and 7.

When using the diaper on a larger child, the flared end 5 of the panel 4 is folded over the stomach of the child, so that the edge 25 of the flared end 5 is more or less vertically aligned with the top edge 11 of the panel. The arms 6 and 7 are folded inwardly into overlapping relationship with the strip 18, and the hook tabs 20 are engaged with the Velcro loop strip 18 to secure the diaper in the closed position.

With the above described structure, changes in the length and width of the diaper are possible.

Figure 2:
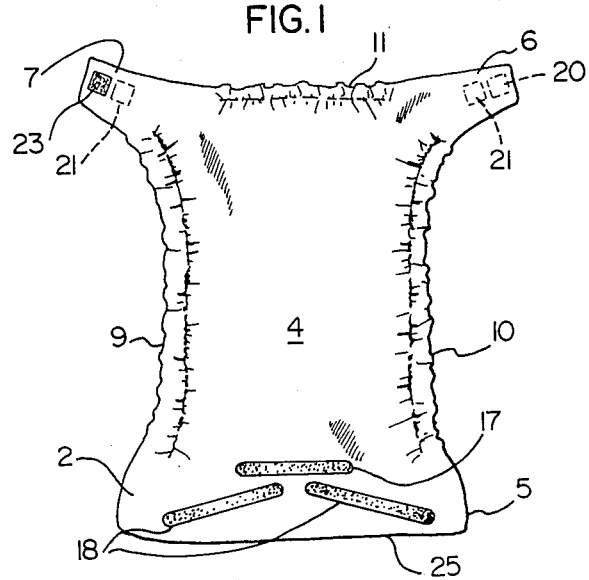
FIG. 2 is a plan view of the outer surface of the diaper of FIG. 1.
Figure 3:
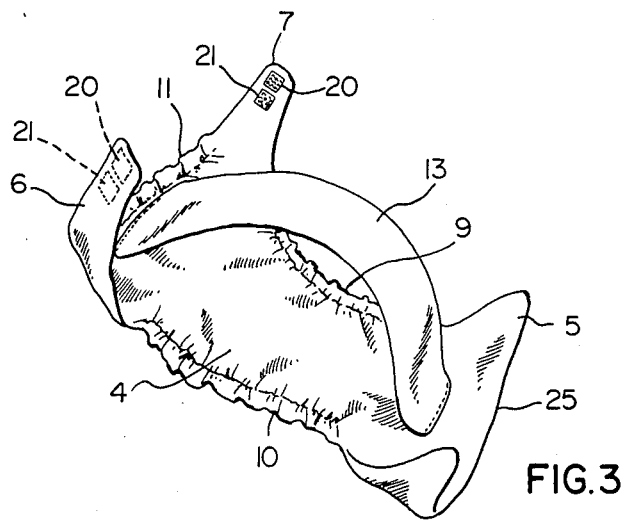
FIG. 3 is a schematic, perspective view of the diaper of FIG. 1 in the open position.

An alternate placement for the Velcro loop strip 18, as seen in FIG. 2 involves cutting the strip 18 into two equal lengths and placing them in a "V" formation. This would permit a more gradual adjustment in the length of the diaper.

During washing the arms 6 and 7 can be folded so that the tab 20 of each arm engages the tab 21 of the same arm, i.e. to protect the hook tabs 20. It will be appreciated that the pad 13 may be connected to the panel 4 at one end only and still serve its stated purpose.

What I claim is:

1. A reusable diaper comprising absorbent panel means having one flared end; arm means extending outwardly from each side of the other end of said panel means; fastener means including hook tab means on the inner surface of each of said arm means for connecting said arm means to said one end when the diaper is in the folded, use position; absorbent pad means having two end edges and two side edges, at least one of said edges being connected to said panel means and two opposite of said edges being unconnected to said panel means, whereby said pad means overlies the inner surface of said panel means in the use position; and the major portion of said pad means is free to facilitate drying of the laundered diaper, said fastener means further including at least two vertically spaced apart fastener strips near the outer bottom end of said panel means when the latter is in the flat, ready for use position; and whereby when the diaper is folded to the use position, the arms can be placed over one of said strip means to couple said hook tab means to one of said strip means, and whereby the length of said diaper may be adjusted by selecting one or the other of said fastener strips.

2. A diaper according to claim 1, wherein only one of said ends of said pad means is connected to said panel means.

3. A diaper according to claim 1, wherein both of said ends of said pad means are connected to said panel means.

4. A diaper according to claim 4, including first fabric tab means on the outer surface of one said arm means, whereby, when the diaper is folded to the use position, the arms can be placed in overlapping relationship to each other to couple one said hook tab means to said first fabric tab means.

5. A diaper as in claim 1 and including three of said fastener strips, a first of said strips being substantially parallel to one end of said panel and spaced therefrom, second and third of said strips being positioned in a V-shape and vertically spaced from said first of said strips, so as to enable vertical length adjustment of said diaper by changing the position of said hook tab means on said second and third strips.

* * * * *